(12) United States Patent
Petereit et al.

(10) Patent No.: US 7,932,258 B2
(45) Date of Patent: *Apr. 26, 2011

(54) USE OF A PARTIALLY NEUTRALIZED, ANIONIC (METH) ACRYLATE COPOLYMER AS A COATING FOR THE PRODUCTION OF A MEDICAMENT PHARMACEUTICAL FORM RELEASING ACTIVE SUBSTANCE AT REDUCED PH VALUES

(75) Inventors: Hans-Ulrich Petereit, Darmstadt (DE); Manfred Assmus, Bickenbach (DE)

(73) Assignee: Evonik Roehm GmbH, Darmstadt (DE)

( * ) Notice: Subject to any disclaimer, the term of this patent is extended or adjusted under 35 U.S.C. 154(b) by 389 days.

This patent is subject to a terminal disclaimer.

(21) Appl. No.: 11/994,440

(22) PCT Filed: Apr. 5, 2006

(86) PCT No.: PCT/EP2006/003115
§ 371 (c)(1),
(2), (4) Date: Jan. 2, 2008

(87) PCT Pub. No.: WO2007/006353
PCT Pub. Date: Jan. 18, 2007

(65) Prior Publication Data
US 2008/0200482 A1 Aug. 21, 2008

(30) Foreign Application Priority Data

Jul. 12, 2005 (DE) .......................... 10 2005 032 806

(51) Int. Cl.
*A61K 31/522* (2006.01)
(52) U.S. Cl. .................. 514/263.3; 424/487; 424/130.1; 424/484; 424/498; 424/490; 424/472
(58) Field of Classification Search .......................... None
See application file for complete search history.

(56) References Cited

U.S. PATENT DOCUMENTS

| 2007/0026082 A1* | 2/2007 | Lizio et al. .................... 424/490 |
| 2008/0044470 A1 | 2/2008 | Petereit et al. |

FOREIGN PATENT DOCUMENTS

| EP | 0 393 747 | 10/1990 |
| EP | 0 636 366 | 2/1995 |
| WO | 00/12064 | 3/2000 |
| WO | 00/33821 | 6/2000 |
| WO | 02/096394 | 12/2002 |
| WO | 03/072087 | 9/2003 |
| WO | 2005/032513 | 4/2005 |
| WO | 2006/087027 | 8/2006 |

OTHER PUBLICATIONS

Gupta et al., "A novel pH—and time-based multi-unit potential colonic drug delivery system. I. Development," International Journal of Pharmaceutics 213 (2001) 83-91.*
U.S. Appl. No. 11/815,632, filed Aug. 6, 2007, Lizio, et al.
U.S. Appl. No. 60/908,855, filed Mar. 29, 2007, Lizio, et al.
U.S. Appl. No. 11/780,915, filed Jul. 20, 2007, Lizio, et al.
U.S. Appl. No. 12/598,138, filed Oct. 29, 2009, Liu, et al.

* cited by examiner

*Primary Examiner* — Yvonne L Eyler
*Assistant Examiner* — Suzanne Ziska
(74) *Attorney, Agent, or Firm* — Oblon, Spivak, McClelland, Maier & Neustadt, L.L.P.

(57) ABSTRACT

The invention relates to the use of a partially neutralized, anionic (meth)acrylate copolymer comprising radically polymerized units of 25 to 95 percent by weight of $C_1$ to $C_4$ alkyl esters of acrylic or methacrylic acid and 5 to 75 percent by weight of (meth)acrylate monomers with an anionic group, at least 4 percent of which are neutralized by means of a base, for producing a medicament that is provided with an active substance-containing core and is coated with the partially neutralized, anionic (meth)acrylate copolymer. The medicament releases at least 30 percent of the active substance contained therein in 30 minutes at a pH at which the active substance is sufficiently soluble and stable and at which the corresponding medicament that is coated with the non-neutralized anionic (meth)acrylate polymer releases less than 10 percent of the active substance contained therein.

16 Claims, No Drawings

USE OF A PARTIALLY NEUTRALIZED, ANIONIC (METH) ACRYLATE COPOLYMER AS A COATING FOR THE PRODUCTION OF A MEDICAMENT PHARMACEUTICAL FORM RELEASING ACTIVE SUBSTANCE AT REDUCED PH VALUES

FIELD OF THE INVENTION

The invention relates to the use of a partially neutralized, anionic (meth)acrylate copolymer as a coating for the production of a pharmaceutical form releasing active substance at reduced pH values.

PRIOR ART

EP 0 088 951 A2 describes a process for coating pharmaceutical forms by means of a coating agent dispersed in water. For the redispersion of carboxyl group-containing (meth) acrylate copolymers from powders to give dispersions, the partial neutralization of the carboxyl groups is recommended. Salt formation of the acidic groups occurs by reaction with a base. Suitable bases are alkalies, such as, for example, sodium hydroxide solution, potassium hydroxide solution, soda, potash, sodium bicarbonate, trisodium phosphate, trisodium citrate or ammonia or physiologically tolerable amines, such as triethanol-amine or tris(hydroxymethyl)aminomethane. A degree of neutralization of 0.1 to 10% by weight of the carboxyl groups contained in the copolymer is favorable with respect to redispersion.

WO 2003/072087 describes a pharmaceutical form and a process for its production. The pharmaceutical form is coated with an anionic (meth)acrylate copolymer which can be partially neutralized if required. In order to prepare a solution of the anionic copolymer, usually a partial or complete neutralization of the acid groups is necessary.

The anionic copolymer, for example, can be stirred gradually into water in a final concentration of 1 to 40% by weight and in the course of this can be partially or completely neutralized by addition of a basic substance such as, for example, NaOH, KOH, ammonium hydroxide or organic bases such as, for example, triethanolamine. It is also possible to employ a powder of the copolymer, to which a base, e.g. NaOH, has already been added during its preparation for the purpose of (partial) neutralization, such that the powder is an already (partially) neutralized polymer. The pH of the solution is usually over 4, e.g. in the range from 4 to about 7.

WO 2004/096185 likewise describes a pharmaceutical form and a process for its production. The pharmaceutical form is coated with an anionic (meth)acrylate copolymer different from that of WO 2003/072087, which can be partially neutralized if required. In order to prepare a solution of the anionic copolymer, usually a partial or complete neutralization of the acid groups is necessary. The anionic copolymer, for example, can be stirred gradually into water in a final concentration of 1 to 40% by weight and in the course of this can be partially or completely neutralized by addition of a basic substance such as, for example, NaOH, KOH, ammonium hydroxide or organic bases such as, for example, triethanolamine. It is also possible to employ a powder of the copolymer, to which a base, e.g. NaOH, has already been added during its preparation for the purpose of (partial) neutralization, such that the powder is an already (partially) neutralized polymer. The pH of the solution is usually over 4, e.g. in the range from 4 to about 7.

OBJECT AND SOLUTION

Anionic (meth)acrylate copolymers, e.g. of the type EUDRAGIT®, EUDRAGIT® L 100-55, EUDRAGIT® S or EUDRAGIT® FS, are known as gastric juice-soluble coatings for pharmaceutical forms. Depending on the monomer composition, but in particular depending on the content of anionic groups, the anionic (meth)acrylate copolymers are characterized by specific dissolution pHs in gastric juice or in artificial gastric juice. Depending on the polymer type, the specific dissolution pHs or the pHs of the specific start of dissolution are in the range from, for example, pH 5.5 to 7.5. Coated pharmaceutical forms thus release the active substance contained from the dissolution pH specific for the respective anionic (meth)acrylate copolymer and above. The specific dissolution pHs thus characterize the start of active substance release.

However, in the transition region from the stomach to the duodenum pH shifts can occur in an unforeseeable due to the influence the of the chyme and of the gastric acid contained therein, which continue into the jejunum. It can therefore occur that an active substance, which theoretically should already be released immediately in the duodenum at a pH of 5.5 or 6.0, is still not released in vivo, because due to food intake in the particular situation the pH is still below the specific dissolution pH of the polymer coating.

For a rapid and complete action of pharmaceuticals, because of its absorption power, the duodenum connecting to the stomach is particularly of interest. In this region of the small intestine, which is characterized by strong motility, the pHs vary between 2 and 6 to be estimated, depending on the content and motility cycle of the stomach. The passage times through the duodenum are short and lie in the range from 15 to 30 min.

For a large number of active substances, e.g. analgesics, a rapid onset of action, synonymous with early absorption in the duodenum, is desired. At the same time, there are a large number of active substances which are adequately soluble and (acid-) stable and are thus theoretically suitable for release in the acidic medium. It would therefore be favorable if the specific dissolution pH of anionic (meth)-acrylate copolymers could be pre-displaced to the acidic region, in order to use these for the coating of pharmaceutical forms which contain active substances having adequate acid stability and in which a rapid absorption is desired.

It is known to employ anionic (meth)acrylate copolymers in partially neutralized form. By this means, an improved solubility of the polymer in water and a stabilization of the polymer dispersions is achieved. As bases for the partial neutralization, usually substances such as NaOH, KOH, ammonium hydroxide or organic bases, such as, for example, triethanolamine, are recommended. The use of partially neutralized, anionic (meth)acrylate copolymers for the selective lowering of the specific dissolution pHs of anionic (meth) acrylate copolymers to the acidic range is not known.

It was therefore seen as the object to make available a pharmaceutical form coated with an anionic (meth)-acrylate copolymer, which is able to release in vitro and in vivo in a comparatively short time a not inconsiderable fraction of the active substance contained even before reaching the specific dissolution pH of the anionic (meth)acrylate copolymer.

The object is achieved by the
use of a partially neutralized, anionic (meth)-acrylate copolymer, consisting of free radical-polymerized units of 40 to 95% by weight of $C_1$- to $C_4$-alkyl esters of acrylic or of methacrylic acid and 5 to 60% by weight of (meth)acrylate monomers having an anionic group, at least 4% of the anionic groups contained being neutralized by means of a base,
for the production of a pharmaceutical form having an active substance-containing core, which is coated with the partially neutralized, anionic (meth)acrylate copolymer and releases at least 30% of the active substance contained in 30 minutes at a pH at which the active substance is adequately soluble and stable and at which a corresponding pharmaceutical form which is coated with the un-neutralized anionic (meth)acrylate copolymer would release less than 10% of the active substance contained in 30 minutes.

ACCOMPLISHMENT OF THE INVENTION

The invention relates to the use of a partially neutralized, anionic (meth)acrylate copolymer, consisting of free radical-polymerized units of 40 to 95% by weight of $C_1$- to $C_4$-alkyl esters of acrylic or of methacrylic acid and 5 to 60% by weight of (meth)acrylate monomers having an anionic group, at least 4%, e.g. 4 to 40% or preferably 4 to 10 or preferably more than 10 to 20% or preferably more than 20 to 40%, of the anionic groups contained being neutralized by means of a base,
for the production of a pharmaceutical form having an active substance-containing core, which is coated with the partially neutralized, anionic (meth)acrylate copolymer and releases at least 30, preferably at least 50, in particular at least 70, % of the active substance contained in 30 minutes at a pH at which the active substance is adequately soluble and stable and at which a corresponding pharmaceutical form which is coated with the un-neutralized anionic (meth)acrylate copolymer releases or would release less than 10, in particular less than 8, preferably less than 5, % of the active substance contained in 30 minutes. The release of active substance can be determined at the respective pH analogously according to USP 28 (see also the examples).

By the neutralization of at least 4%, preferably 4 to 40% or preferably 4 to 10 or preferably more than 10 to 20% or preferably more than 20 to 40% of the anionic groups contained, the specific dissolution pH of the (meth)acrylate copolymer, depending on the degree of neutralization, can be lowered or decreased by 0.5 to 1.5, preferably more than 1.5 to 2.5 or by more than 2.5 to 3.5, pH units. Depending on the active substance, the suitable variant can be chosen in order to guarantee release of active substance at the correspondingly decreased pH.

Anionic (Meth)Acrylate Copolymer

The anionic (meth)acrylate copolymer consists to 25 to 95, preferably to 40 to 95, in particular to 60 to 40, % by weight of free radical-polymerized $C_1$- to $C_4$-alkyl esters of acrylic or of methacrylic acid and to 75 to 5, preferably 60 to 5, in particular 40 to 60, % by weight of (meth)acrylate monomers having an anionic group.

Usually, the amounts mentioned add up to 100% by weight. Additionally, however, without this leading to an adverse effect on or change in the essential properties, small amounts in the range from 0 to 10, e.g. 1 to 5, % by weight, of further vinylically copolymerizable monomers, such as, for example, hydroxyethyl methacrylate or hydroxyethyl acrylate can be contained. Preferably, no further vinylically copolymerizable monomers are contained.

$C_1$- to $C_4$-alkyl esters of acrylic or of methacrylic acid are in particular methyl methacrylate, ethyl meth-acrylate, butyl methacrylate, methyl acrylate, ethyl acrylate and butyl acrylate.

A (meth)acrylate monomer having an anionic group is, for example, acrylic acid; methacrylic acid is preferred.

Suitable copolymers for the purposes of the invention are in particular anionic (meth)acrylate copolymers of 40 to 60% by weight of methacrylic acid and 60 to 40% by weight of methyl methacrylate or 60 to 40% by weight of ethyl acrylate (EUDRAGIT® L or EUDRAGIT® L 100-55 types). By partial neutralization of at least 4%, preferably 4 to 40% or preferably 4 to 10 or preferably more than 10 to 20% or preferably more than 20 to 40% of the anionic groups contained, depending on the degree of neutralization, the specific dissolution pH can be lowered by 0.5 to 3.5 pH units.

EUDRAGIT® L is a copolymer of 50% by weight of methyl methacrylate and 50% by weight of methacrylic acid. The pH of the start of specific active substance release in intestinal juice or artificial intestinal juice (specific dissolution pH) can be stated as pH 6.0. By partial neutralization of at least 4%, preferably 4 to 40% or preferably 4 to 10 or preferably more than 10 to 20% or preferably more than 20 to 40% of the anionic groups contained, depending on the degree of neutralization, the specific dissolution pH can be lowered by 0.5 to 3.5 pH units.

EUDRAGIT® L 100-55 is a copolymer of 50% by weight of ethyl acrylate and 50% by weight of methacrylic acid.

EUDRAGIT® L 30D-55 is a dispersion comprising 30% by weight of EUDRAGIT® L 100-55. The pH of the start of specific active substance release in intestinal juice or artificial intestinal juice (specific dissolution pH) can be stated as pH 5.5. By partial neutralization of at least 4%, preferably 4 to 40% or preferably 4 to 10 or preferably more than 10 to 20% or preferably more than 20 to 40% of the anionic groups contained, depending on the degree of neutralization, the specific dissolution pH can be lowered by 0.5 to 3.5 pH units.

Copolymers likewise suitable are anionic (meth)acrylate copolymers of 20 to 40% by weight of methacrylic acid and 80 to 60% by weight of methyl methacrylate (EUDRAGIT® S type). By neutralization of at least 4%, preferably 4 to 40% or preferably 4 to 10 or preferably more than 10 to 20% or preferably more than 20 to 40% of the anionic groups contained, depending on the degree of neutralization, the specific dissolution pH can be lowered by 0.5 to 3.5 pH units.

EUDRAGIT® S 100 is a copolymer of 30% by weight of methacrylic acid and 70% by weight of methyl methacrylate. The pH of the start of specific active substance release in intestinal juice or artificial intestinal juice (specific dissolution pH) can be stated as pH 7.0.

Copolymers likewise suitable for the purposes of the invention are (meth)acrylate copolymers consisting of 10 to 30% by weight of methyl methacrylate, 50 to 70% by weight of methyl acrylate and 5 to 15% by weight of methacrylic acid (EUDRAGIT® FS type, see EP 0 704 208 B1). By neutralization of at least 4%, preferably 4 to 40% or preferably 4 to 10 or preferably more than 10 to 20% or preferably more than 20 to 40% of the anionic groups contained, depending on the degree of neutralization, the specific dissolution pH can be lowered by 0.5 to 3.5 pH units.

EUDRAGIT® FS 30 D is a dispersion comprising 30% by weight of a copolymer of 25% by weight of methyl methacrylate, 65% by weight of methyl acrylate and 10% by weight of methacrylic acid. The pH of the start of specific active substance release in intestinal juice or artificial intestinal juice (specific dissolution pH) can be stated as pH 7.0.

A copolymer (see WO 2003/072087) furthermore suitable for the purposes of the invention is one which is composed of
   20 to 34% by weight of methacrylic acid and/or acrylic acid,
   20 to 69% by weight of methyl acrylate and
   0 to 40% by weight of ethyl acrylate and/or optionally
   0 to 10% by weight of further vinylically copolymerizable monomers,
with the proviso that the glass transition temperature of the copolymer according to ISO 11357-2, item 3.3.3, is at most 60° C. Because of its good extension at break properties, this (meth)acrylate copolymer is suitable in particular for the compression of pellets to give tablets. By neutralization, at least 4%, preferably 4 to 40% or preferably 4 to 10 or preferably more than 10 to 20% or preferably more than 20 to 40% of the anionic groups contained, depending on the degree of neutralization, can be lowered by 0.5 to 3.5 pH units to the specific dissolution pH.

Copolymers (see WO 2004/096185) furthermore suitable for the purposes of the invention are those which are composed of
- 20 to 33% by weight of methacrylic acid and/or acrylic acid,
- 5 to 30% by weight of methyl acrylate and
- 20 to 40% by weight of ethyl acrylate and
- greater than 10 to 30% by weight of butyl methacrylate and optionally
- 0 to 10% by weight of further vinylically copolymerizable monomers, where the amounts of the monomers add up to 100% by weight, with the proviso that the glass transition temperature of the copolymer according to ISO 11357-2, item 3.3.3 (midpoint temperature $T_{mg}$), is 55 to 70° C. Because of its good mechanical properties, copolymers of this type are suitable in particular for the compression of pellets to give tablets. By neutralization, at least 4%, preferably 4 to 40% or preferably 4 to 10 or preferably more than 10 to 20% or preferably more than 20 to 40% of the anionic groups contained, depending on the degree of neutralization, can be lowered by 0.5 to 3.5 pH units to the specific dissolution pH.

The abovementioned copolymer is composed in particular together of free radical-polymerized units of
- 20 to 33, preferably 25 to 32, particularly preferably 28 to 31, % by weight of methacrylic acid or acrylic acid; methacrylic acid is preferred,
- 5 to 30, preferably 10 to 28, particularly preferably 15 to 25, % by weight of methyl acrylate,
- 20 to 40, preferably 25 to 35, particularly preferably 18 to 22, % by weight of ethyl acrylate, and
- greater than 10 to 30, preferably 15 to 25, particularly preferably 18 to 22, % by weight of butyl methacrylate, the monomer composition being chosen such that the glass transition temperature of the copolymer is 55 to 70° C., preferably 59 to 66, particularly preferably 60 to 65, ° C.

For the adjustment of special release profiles or release sites, mixtures of the copolymers mentioned can also be used.

Glass transition temperature is understood here as meaning in particular the midpoint temperature $T_{mg}$ according to ISO 11357-2, item 3.3.3. The measurement is carried out without plasticizer addition, at residual monomer contents (REMO) of less than 100 ppm, at a heating rate of 10° C./min and under a nitrogen atmosphere.

The copolymer preferably consists essentially to exclusively, to 90, 95 or 99 to 100% by weight, of the monomers methacrylic acid, methyl acrylate, ethyl acrylate and butyl methacrylate in the ranges of amounts indicated above.

Additionally, however, without this having to lead to an adverse effect on the essential properties, small amounts in the range from 0 to 10, e.g. 1 to 5% by weight, of further vinylically copolymerizable monomers, such as, for example, methyl methacrylate, butyl acrylate, hydroxyethyl methacrylate, vinyl-pyrrolidone, vinylmalonic acid, styrene, vinyl alcohol, vinyl acetate and/or their derivatives can be present.

Preparation of the Anionic (Meth)Acrylate Copolymers

The anionic (meth)acrylate copolymers can be prepared in a manner known per se by free-radical polymerization of the monomers (see, for example, EP 0 704 207 A2, EP 0 704 208 A2, WO 2003/072087, WO 2004/096185). The copolymers can be prepared in a manner known per se by free-radical emulsion polymerization in aqueous phase in the presence of preferably anionic emulsifiers, for example according to the process described in DE-C 2 135 073.

The copolymer can be prepared continuously or batchwise (batch process) in substance, in solution, by bead polymerization or in emulsion by customary processes of free-radical polymerization in the presence of free-radical-forming initiators and optionally regulators for the adjustment of the molecular weight. The mean molecular weight Mw (weight average, determined, for example, by measurement of the solution viscosity) can lie, for example, in the range from 80,000 to 1,000,000 (g/mol). Preferably, the emulsion polymerization is in aqueous phase in the presence of water-soluble initiators and (preferably anionic) emulsifiers.

In the case of substance polymerization, the copolymer can be obtained in solid form by breaking, extrusion, granulating or die-face cutting.

The (meth)acrylate copolymers are obtained in a manner known per se by free-radical substance, solution, bead or emulsion polymerization. They must be brought to the particle size range according to the invention before processing by suitable grinding, drying or spray processes. This can be carried out by simple breaking of extruded and cooled granule strips or die-face cutting.

In particular when mixing with further powders or liquids, the use of powders can be advantageous. Suitable implements for the production of the powders are familiar to the person skilled in the art, e.g. air jet mills, pinned disk mills, fan mills. If desired, appropriate screening steps can be included. A suitable mill for large industrial amounts is, for example, a reverse jet mill (Multi no. 4200), which is operated at about 6 bar overpressure.

Partial Neutralization

The invention relates to the use of a partially neutralized anionic (meth)acrylate copolymer, consisting of free radical-polymerized units of 40 to 95% by weight of $C_1$- to $C_4$-alkyl esters of acrylic or of methacrylic acid and 5 to 60% by weight of (meth)acrylate monomers having an anionic group, at least 8%, preferably 8 to 60% or more than 10 to 50%, particularly preferably 12 to 40, in particular more than 15 to 35% of the anionic groups contained being neutralized by means of a base.

Bases, in particular inorganic bases, preferably those having a molecular weight of at most 150, are suitable for the inventive partial neutralization of the (meth)acrylate copolymers. Suitable bases are in particular, for example, sodium hydroxide solution (NaOH), potassium hydroxide solution (KOH), ammonium hydroxide or organic bases such as, for example, triethanolamine, soda, potash, sodium bicarbonate, trisodium phosphate, trisodium citrate or ammonia or physiologically tolerable amines, such as triethanolamine or tris-(hydroxymethyl)aminomethane. NaOH is particularly preferred.

The molecular weight of the substances mentioned is known or can be calculated by means of the atomic weights by means of the atoms present in the molecule.

Cationic, organic bases having an Mw greater than 150 are not suitable or are expressly excluded from the invention, because these influence the active substance release behavior in another manner not according to the invention. Those to be excluded are, inter alia, natural or synthetic oligomers or polymers, e.g. of 3 to 100, preferably 5 to 25, units, of histidine, arginine or lysine, polyhistidines, polyarginines, polylysines, cationic or zwitterionic phospholipids, such as, for example, phosphatidylcholine, ribonucleosides: condensation products of the hydroxyl function on carbon atom 1 of ribose with the heterocyclic amino function of the bases adenine, guanine, cytosine, thymine or uracil, corresponding to the occurrence in the RNA; deoxyribonucleosides: condensation products of the hydroxyl function on carbon atom 1 of deoxyribose with the heterocyclic amino function of the bases adenine, guanine, cytosine, thymine or uracil, corresponding to the occurrence in the DNA; bases consisting of cationic surface-active auxiliaries or emulsifiers, such as benzalkonium (CAS RN: 8001-54-5), benzethonium (CAS 121-54-0), cetalkonium (CAS 122-18-9), cetrimide (CAS 8044-71-1), cetrimonium (CAS 57-09-0), cetylpyridinium (CAS 123-03-5), stearalkonium (CAS 122-19-0), diallyldimethyl-ammonium (CAS 230-993-8).

Dispersions

The partially neutralized (meth)acrylate copolymer can be present, for example, in the form of an aqueous dispersion having a 10 to 50 percent solids content.

The partially neutralized (meth)acrylate copolymer can be present in the form of a redispersible powder which has been obtained from a dispersion, e.g. by spray drying.

Dispersions/Partial Neutralization

The emulsion polymer is preferably prepared and used in the form of a 10 to 50% by weight, in particular 20 to 40%, aqueous dispersion. As the commercial form, a solids content of 30% by weight is preferred. The weight-average latex particle size (radius) is usually 40 to 100 nm, preferably 50 to 70 nm, which guarantees a process technology-favorable viscosity of below 1000 mPa·s. The particle size can be determined by laser diffraction, e.g. using the Mastersizer 2000 (Malvern).

The anionic copolymer, for example, can be gradually stirred into water in a final concentration of 1 to 40% by weight and in the course of this, as described, partially by addition of a basic substance according to the invention, such as, for example, NaOH. It is also possible to employ a powder of the copolymer, to which a base, for example NaOH, has already been added during its preparation for the purpose of (partial) neutralization, such that the powder is an already (partially) neutralized polymer. The pH of the solution is usually over 4, e.g. in the range from 4 to about 6. It is also possible here to carry out, for example, mixtures of batches of fully or partially neutralized dispersions with un-neutralized dispersions or mixtures of batches having a different degree of partial neutralization and to further process them in the manner described, i.e. use the mixture for coatings or first freeze- or spray-dry to give a powder. Likewise possible is the mixing of a powder of un-neutralized polymer with an appropriate amount of solid base, such that the neutralization results only on redispersion in water.

The dispersion, for example, can also be spray-dried or freeze-dried in a manner known per se and made available in the form of a redispersible powder (see, for example, EP-A 0 262 326). Alternative processes are the freeze drying or coagulation and squeezing off of the water in an extruder with subsequent granulation (see, for example, EP-A 0 683 028).

Copolymer dispersions of spray- or freeze-dried and redispersible powders can have an increased shear stability. This is advantageous, in particular, on spray application. The shear stability can be increased by addition of emulsifiers. Preferably, an anionic emulsifier is present in an amount from 0.1 to 2% by weight. Sodium laurylsulfate is particularly preferred as an emulsifier.

Use of the Partially Neutralized (Meth)Acrylate Copolymer

The partially neutralized, anionic (meth)acrylate copolymer can be used according to the invention for the production of a pharmaceutical form having an active substance-containing core which is coated with the partially neutralized anionic (meth)acrylate copolymer and releases at least 30% of the active substance contained in 30 minutes at a pH at which the active substance is adequately soluble and stable and at which an appropriate pharmaceutical form which is coated with the un-neutralized anionic (meth)acrylate copolymer would release less than 10% of the active substance contained in 30 minutes.

The release test according to USP 28, in particular according to USP 28 <711> paddle method (=apparatus 2) is adequately known to the person skilled in the art.

The active substance release can analogously be determined according to USP 28, in particular USP 28-NF 23, general chapter <711>, dissolution, apparatus 2 (paddle), method <724>"Delayed Release (Enteric Coated) Articles—General General Drug Release Standard", method B (100 rpm, 37° C.) with the following modification: In analogy to USP 28, the coated pharmaceutical forms are tested for active substance release in buffer solutions at the pH relevant in each case. The active substance concentration in the test medium can be determined depending on the active substance, e.g. photometrically or by means of HPLC (high pressure liquid chromatography).

Mixtures with Further Film-Forming Polymers

The coating of the pharmaceutical form can contain, additionally to that of a partially neutralized, anionic (meth)acrylate copolymer, up to 50, preferably up to 30, in particular up to 20, % by weight of further film-forming polymers which contain no or only insignificant amounts of ionic side groups. Insignificant amounts of ionic side groups are present in the polymer if altogether less than 5%, e.g. 0.1 to less than 5%, of the side groups or of the monomer units contain ionic groups.

Further film-forming polymers which contain no or only insignificant amounts of ionic side groups can be: copolymers of methyl methacrylate and ethyl acrylate (EUDRAGIT® NE30D), polyvinyl alcohol-polyethylene glycol graft copolymer (Kollicoat® IR), polyvinyl acetate (PVAc, Kollicoat® SR), hydroxyethyl-cellulose (HEC, Klucel®), hydroxypropylcellulose (HPC), hydroxypropylmethylcellulose (HPMC, Pharmacoat®, Methocel®, Sepifilm®, Viscontran®, Opadry®), hydroxy-methylethylcellulose (HEMC), ethylcellulose (EC, Ethocel®, Aquacoat®, Surelease®), methylcellulose (MC, Viscontran®, Tylopur®, Methocel®), cellulose esters or a mixture of the polymers mentioned.

Auxiliaries

Customary additives for the construction of the core and for the coating are preferably added to the formulation according to use during its preparation. In principle, of course, all substances employed must be toxicologically harmless and, in particular in medicaments, without risk for patients.

Amounts used and use of the customary additives in pharmaceutical films or coatings are familiar to the person skilled in the art. Customary additives can be, for example, mold release agents, pigments, stabilizers, antioxidants, pore-forming agents, penetration promoters, lustering agents, aromatic substances or flavorings. They serve as processing auxiliaries and should guarantee a safe and reproducible preparation process and good long-term storage stability or they achieve additional advantageous properties in the pharmaceutical form.

Plasticizers

Substances suitable as plasticizers usually have a molecular weight between 100 and 20,000 and contain one or more hydrophilic groups in the molecule, e.g. hydroxyl, ester or amino groups. Citrates, phthalates, sebacates and castor oil are suitable. Examples of suitable plasticizers are citric acid alkyl esters, propylene glycol, glycerol esters, phthalic acid alkyl esters, sebacic acid alkyl esters, sucrose esters, sorbitan esters, diethyl sebacate, dibutyl sebacate and polyethylene glycols 4000 to 20,000. Preferred plasticizers are tributyl citrate, triethyl citrate, acetyltriethyl citrate, dibutyl sebacate and diethyl sebacate. The amounts used are between 1 and 35, preferably 5 to 25, % by weight, based on the partially neutralized (meth)acrylate copolymer.

The addition of the plasticizers to the formulation can be carried out in a known manner, directly, in aqueous solution or after heat pretreatment of the mixture. Mixtures of plasticizers can also be employed.

Mold Release Agents:

Mold release agents usually have lipophilic properties and are usually added to the spray suspensions. They prevent agglomeration of the cores during film-coating. Preferably, talc, Mg or Ca stearate, ground silicic acid, kaolin or nonionic emulsifiers having an HLB between 3 and 8 are employed. Customary amounts used for mold release agents are between 0.5 to 100% by weight based on the polymer or the polymer mixture.

Pigments:

Pigments serve for the coloring of the film.

Pigments can be added directly to the (meth)acrylate copolymer dispersion, e.g. by stirring in, or also dispersed separately and then added to the dispersion. Customary amounts used are, for example, 20 to 400% by weight, based on the weight of the polymer or of the polymer mixture.

For this, for example, see also: Deutsche Forschungs-gemeinschaft, *Farbstoffe für Lebensmittel* [Colorants for Foodstuffs], Harald Boldt Verlag K G, Boppard (1978); Deutsche Lebensmittelrundschau 74, No. 4, p. 156 (1978); Pharmaceutical Colorant Directive AmFarbV of Aug. 25, 1980.

Suitable pigments can be, for example, aluminum oxide pigments or iron oxide pigments. Those suitable are, for example, Yellow Orange, Cochineal Red Lake, color pigments based on aluminum oxide or azo dyes, sulfonic acid dyes, Yellow Orange S (E110, C.I. 15985, FD&C Yellow 6), Indigocarmine (E132, C.I. 73015, FD&C Blue 2), Tartrazine (E 102, C.I. 19140, FD&C Yellow 5), Ponceau 4R (E 125, C.I. 16255, FD&C Cochineal Red A), Quinoline Yellow (E 104, C.I. 47005, FD&C Yellow 10), Erythrosine (E127, C.I. 45430, FD&C Red 3), Azorubine (E 122, C.I. 14720, FD&C Carmoisine), Amaranth (E 123, C.I. 16185, FD&C Red 2), Brilliant Acid Green (E 142, C.I. 44090, FD&C Green S).

The E numbers of the pigments indicated refer to EU numbering. For this, see also "Deutsche Forschungs-gemeinschaft, *Farbstoffe für Lebensmittel*, Harald Boldt Verlag K G, Boppard (1978); Deutsche Lebensmittel-rundschau 74, No. 4, p. 156 (1978);

Pharmaceutical Colorant Directive AmFarbV of Aug. 25, 1980. The FD&C numbers refer to licensing in Food, Drugs and Cosmetics by U.S. Food and Drug Administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Pharmaceutical Form According to Use

The invention relates to the use of a partially neutralized, anionic (meth)acrylate copolymer, consisting of free radical-polymerized units of 40 to 95% by weight of $C_1$- to $C_4$-alkyl esters of acrylic or of methacrylic acid and 5 to 60% by weight of (meth)acrylate monomers having an anionic group, at least 4%, e.g. 4 to 40% or preferably 4 to 10 or preferably more than 10 to 20% or preferably more than 20 to 40%, of the anionic groups contained being neutralized by means of a base, for the production of a pharmaceutical form having an active substance-containing core, which is coated with the partially neutralized, anionic (meth)acrylate copolymer and releases at least 30% of the active substance contained in 30 minutes at a pH at which the active substance is adequately stable and at which a corresponding pharmaceutical form which is coated with the un-neutralized anionic (meth)acrylate copolymer would release less than 10% of the active substance contained in 30 minutes.

The pharmaceutical form can preferably contain a polymer film having NaOH as a neutralizing agent in combination with 5 to 25% by weight of a plasticizer.

Active Substances

According to use, a pharmaceutical form having an active substance-containing core is obtained, which is covered with the partially neutralized anionic (meth)-acrylate copolymer and releases at least 30% of the active substance contained in 30 minutes at a pH at which the active substance is adequately soluble and stable.

A pharmaceutical form according to use can be covered (see Ex. C), for example, with a EUDRAGIT® L 100-55 (copolymer of 50% by weight of ethyl acrylate and 50% by weight of methacrylic acid; spec dissolution pH pH 5.5) partially neutralized with NaOH to 15%. In this case, significant amounts of the active substance contained are released even at pH 4.0. The active substance contained must therefore be adequately soluble and stable at pH 4.0 in order that the intended therapeutic action can start.

Adequately soluble is understood according to the Guidance for Industry "Waiver of In Vivo Bioavailability and Bioequivalence Studies for Immediate-Release Solid Oral Dosage Forms Based on a Biopharmaceutics Classification" by U.S. Department of Health and Human Services—Food And Drug Administration—Center for Drug Evaluation and Research CDER), August 2000, BP system" Section II.A—Solubility as meaning that a pharmaceutical dose dissolves in 250 ml of a buffer solution having the pH relevant in each case independently of its absolute amount. The relevant pHs would be pH 4.0 in the above example. The solubility is preferably determined analogously to the procedure in Section III A.

Adequately stable is understood as meaning when the active substance contained remains therapeutically active or chemically unchanged to a buffer solution having the pH relevant in each case at 37° C. over 2 hours to a proportion of at least 90, preferably of at least 95, %, where a possibly decomposed or therapeutically inactive proportion must not be toxic or intolerable. The pH-dependent stability can be checked by physicochemical analysis, and also by in-vitro or in-vivo studies. For a large number of customary active substances, appropriate data are already available. Acetylsalicylic acid is adequately soluble and stable, for example, at pH 4.0.

Suitable active substances for the purposes of the invention are, for example, those active substances whose commercial forms have enteric coatings because the active substances are insoluble or unstable at pH 1.2, but of which it is known that they are adequately soluble and stable from approximately pH 3.0. The advantageous effect of the invention stands out, in particular, with those active substances in which a particularly rapid action is indicated.

A selection of potentially suitable active substances of this type can be, for example: proton pump blockers, in particular omeprazole, lanzoprazole, pantoprazole, rabeprazole, perprazole, esomprazole, tenatoprazole, anastrozole, aripiprazole, dapriprazole, hydroxy-omeprazole, leminoprazole, and paroxetine, pindolol, reboxetine, antibiotics, in particular 5-aminosalicylic acid, sulfasalazine budenoside, natamycin, preglumetacin, sulfasalacine, nitrofurantion, didanosine, nonsteroidal antirheumatics, in particular acetylsalicylic acid, acemetacin, ibuprofen, diclofenac, naproxen, ketoprofen, dexketo-profen, indometacin, tiaprofenic acid, and lipid-lowering agents, in particular pravastatin, anticonvulsants, in particular valproic acid, or antihypertensives, such as, for example, ramipril and its salts.

Mention may furthermore be made of enzyme, protein or peptide active substances such as, for example: bromelain, pancreatine or trypsin, an insulin, a human growth hormone (hGH), corbaplatin, intron A, calcitonin, cromalyn, an interferon, a calcitonin, granulocyte colony stimulating factor (G-CSF), an interleukin, a kinin, parathyroid hormones, glucagon, pro-somatostatin, a somatostatin, detirelix, cetrorelix, vasopressin, 1-deaminocysteine-8-D-arginine-vasopressin, leuprolide acetate or an antigen which has been obtained from grasses or other plants, such as, for example, rye, wheat, barley, oats, Bermuda grass, horsetail, maple, elm, oak, plane, poplar, cedar, horsetail or thistles, IgG, specific vaccines or monoclonal antibodies, a peptide hormone, an immunomodulatory protein, an antigen or antibody.

Further active substances in which the invention can advantageously be employed are: oligonucleotides or anionic active substances having a $pK_a$ value in a range in question.

Process for the Production of a Pharmaceutical Form According to Use

The pharmaceutical form according to use can in a manner known per se by means of pharmaceutically customary processes, such as direct compression, compression of dry, moist or sintered granules, extrusion and subsequent rounding, moist or dry granulation or direct pelleting or by binding of powders (powder layering) to active substance-free beads or neutral cores (nonpareilles) or active substance-containing particles and by means of application of the polymer coating in the spray process or by fluidized bed granulation.

The layer thickness of the coating is without significant influence on the release pH over wide ranges. Customary application amounts are between 4 and 10 mg/polymer per $cm^2$ core surface area.

Production of Multiparticulate Pharmaceutical Forms

The invention is also suitable for the production of multiparticulate pharmaceutical forms, since the copolymers to be used withstand the high pressures on compression of the pellets with the filler.

The preparation of multiparticulate pharmaceutical forms by compression of a pharmaceutically customary binder with active substance-containing particles is described in detail, for example, in Beckert et al. (1996), "Compression of enteric-coated pellets to disintegrating tablets", *International Journal of Pharmaceutics* 143, p. 13-23, and in WO 96/01624.

Active substance-containing pellets can be prepared by applying an active substance by means of a layering process. For this, active substance is homogenized together with further auxiliaries (mold release agents, optionally plasticizers) and dissolved or suspended in a binder. By means of a fluidized bed process, the liquid can be applied to placebo pellets or other suitable carrier materials, the solvent or suspending agent being evaporated (literature: *International Journal of Pharmaceutics* 143, p. 13-23). After the preparation process, a drying step can be added. The active substance can be applied in a number of layers.

Some active substances, e.g. acetylsalicylic acid, are commercially available in the form of active substance crystals and can be employed in this form instead of active substance-containing pellets.

Film coatings on active substance-containing pellets are customarily applied in fluidized bed apparatuses. Formulation examples are mentioned in this application. Film-forming agents are customarily mixed with plasticizers and mold release agents according to a suitable process. The film-forming agents can be present here as a solution or suspension. The auxiliaries for the film formation can likewise be dissolved or suspended. Organic or aqueous solvents or dispersants can be used. Stabilizers can additionally be used for the stabilization of the dispersion (example: polysorbate 80 or other suitable emulsifiers or stabilizers).

Examples of mold release agents are glycerol monostearate or other suitable fatty acid derivatives, silicic acid derivatives or talc. Examples of plasticizers are propylene glycol, phthalates, polyethylene glycols, sebacates or citrates, and other substances mentioned in the literature.

Between the active substance-containing and intestine-soluble copolymer layer, a separating layer can be applied which serves for the separation of active substance and coating material for the purpose of preventing interactions. This layer can consist of inert film-forming agents (e.g. HPMC, HPC or (meth)acrylic acid copolymers) or, for example, talc or other suitable pharmaceutical substances. Likewise, combinations of film-forming agents and talc or similar substances can be used.

Mixtures for the production of tablets from coated particles are prepared by mixing the pellets with suitable binders for tabletting, if necessary the addition of disintegration-promoting substances and if necessary the addition of lubricants. Mixing can take place in suitable machines. Mixers which lead to damage to the coated particles are unsuitable, e.g. ploughshare mixers. To achieve suitable short disintegration times, a specific sequence in the addition of the auxiliaries to the coated particles may be necessary. By premixing with the coated particles with the lubricant or mold release agent magnesium stearate, its surface can be hydrophobized and thus agglutination can be avoided.

Mixtures suitable for tabletting customarily contain 3 to 15% by weight of a disintegrant, e.g. Kollidon C L, and, for example, 0.1 to 1% by weight of a lubricant and mold release agent such as magnesium stearate. The proportion of binder is determined by the required proportion of coated particles.

Typical binders are, for example, Cellactose®, microcrystalline cellulose, calcium phosphates, Ludipress®, lactose or other suitable sugars, calcium sulfates or starch derivatives. Substances of low bulk density are preferred.

Typical disintegrants (blasting agents) are crosslinked starch or cellulose derivatives, and crosslinked polyvinylpyrrolidone. Cellulose derivatives are likewise suitable. By choice of a suitable binder, the use of disintegrants can be omitted.

Typical lubricants and mold release agents are magnesium stearate or other suitable salts of fatty acids or substances mentioned in the literature for this purpose (e.g. lauric acid, calcium stearate, talc etc.). When using suitable machines (e.g. a tablet press with external lubrication) or suitable formulations, the use of a lubricant and mold release agent in the mixture can be omitted.

An auxiliary can optionally be added to the mixture to improve flow (e.g. highly disperse silicic acid derivatives, talc etc.).

Tabletting can be carried out in customary tablet presses, eccentric or rotary tablet presses, at compressive forces in the range from 5 to 40 kN, preferably 10-20 kN. The tablet presses can be equipped with systems for external lubrication. Optionally, special systems are used for filling matrices, which avoid matrix filling by means of stirrer bars.

The layer thickness of the coating is without significant influence on the release pH over wide ranges. Customary application amounts are between 4 and 10 mg/polymer per $cm^2$ of core surface.

Further Production Processes for the Pharmaceutical Form According to Use

Application process takes place by means of spray application from organic solution, or preferably by means of spray application from aqueous dispersions, by melting or by direct powder application. For quality, it is crucial here that uniform, pore-free coatings result.

For application processes according to the prior art see, for example, Bauer, Lehmann, Osterwald, Rothgang, "Uberzogene Arzneiformen" [Coated Pharmaceutical Forms] Wissenschaftliche Verlagsgesellschaft mbH Stuttgart, chap. 7, pp. 165-196.

Relevant properties, tests required and specifications for application are listed in pharmacopeias.

Details can be taken from the customary textbooks, e.g.:

Voigt, R. (1984): Lehrbuch der pharmazeutischen Technologie [Textbook of Pharmaceutical Technology]; Verlag Chemie Weinheim—Beerfield Beach/Fla.—Basle.

Sucker, H., Fuchs, P., Speiser, P.: Pharmazeutische Technologie [Pharmaceutical Technology], Georg Thieme Stuttgart (1991), in particular chapters 15 and 16, pp. 626-642.

Gennaro, A., R. (Editor), Remington's Pharmaceutical Sciences, Mack Publishing Co., Easton Pa. (1985), Chapter 88, pp. 1567-1573.

List, P. H. (1982): Arzneiformenlehre [Pharmaceutical Forms Theory], Wissenschaftliche Verlagsgesellschaft mbH, Stuttgart.

Covering Layer

It is also possible to apply an outer covering layer (topcoat) of a further, preferably water-soluble, polymer and auxiliaries, e.g. pigments and/or mold release agents, which guarantees further functions, such as, for example, coloring or prevention of agglutination.

Separating Layer

Between the active substance-containing and intestine-soluble copolymer layer, a separating layer (subcoat) can be applied which serves for the separation of active substance and coating material for the purposes of the prevention of interactions. This layer can consist of inert film-forming agents (e.g. HPMC, HPC or (meth)acrylic acid copolymers) or, for example, talc or other suitable pharmaceutical substances. Likewise, combinations of film-forming agents and talc or similar substances can be used.

EXAMPLES

Coating with EUDRAGIT® L 100-55 (copolymer of 50% by weight of ethyl acrylate and 50% by weight of methacrylic acid) from 30% strength dispersion (EUDRAGIT® L 30D-55). Specific dissolution pH=pH 5.5. Partial neutralization with NaOH.

In examples A to D, theophylline granules, particle size 0.5 to 0.8 mm were coated with non-neutralized and with differently partially neutralized polymers in a fluidized bed apparatus at product temperatures between 30 and 35° C. The polymer application in all experiments was between 18 and 25% by weight, based on the core weight.

Formulation

Example A

| | Amount | Solid | % solid |
|---|---|---|---|
| EUDRAGIT ® L 30D-55 | 794.1 g | 238.2 g | 30.0 |
| Talc | 119.1 g | 119.1 g | 50.0 |
| Triethyl citrate | 23.8 g | 23.8 g | 10.0 |
| Water | 1456.7 g | | |

In examples B, C and D, as opposed to example A, 1N NaOH was added in an appropriate amount in order to neutralize 4.4, 15 or 30% of the carboxyl groups of EUDRAGIT® L 30D-55.

After spray application, the particles were dried at 40° C. on drying racks for 2 hours.

Release Test of Theophylline Pellets According to USP 28 <711> Paddle Method (=Apparatus 2)

The coated theophylline particles were tested at 100 rpm according to USP 28 <711> paddle method (=Apparatus 2).

Subsequently, the active substance release was tested analogously to USP 28 at constant pH using the following buffer compositions (Table 1). The active substance release after 30 min was determined photometrically (see Table 2).

TABLE 1

| | pH 2 | pH 3 | pH 4 | pH 5 | pH 6 |
|---|---|---|---|---|---|
| $H_3PO_4$ 0.1 M | 2210 g | 680 g | 553 g | 509 g | 332 g |
| NaCl | 42.5 g | 42.5 g | 42.5 g | 42.5 g | 42.5 g |
| $KH_2PO_4$ | 5 g | 5 g | 5 g | 5 g | 5 g |
| $K_2HPO_4$ | 10 g | 10 g | 10 g | 10 g | 10 g |
| water to | 5000 ml | 5000 ml | 5000 ml | 5000 ml | 5000 ml |

Examples A: not according to the invention. Example A serves as a comparison for the examples B, C and D according to the invention.

EUDRAGIT® L 30D-55: Specific dissolution pH=pH 5.5

TABLE 2

| | Example | | | |
|---|---|---|---|---|
| | A comparison | B acc. to the invention | C acc. to the invention | D acc. to the invention |
| | EUDRAGIT ® L 100-55 (copolymer of 50% by weight of ethyl acrylate and 50% by weight of methacrylic acid): Spec. dissolution pH = pH 5.5 Degree of neutralization [%] | | | |
| pH | 0 | 4.4 | 15 | 30 |
| | Active substance release [%] after 30 minutes | | | |
| 2.0 | 0 | 0 | 0 | 6 |
| 3.0 | 0 | 0 | 5 | 35 |
| 4.0 | 0 | 3 | 35 | 95 |
| 5.0 | 0 | 33 | 70 | 99 |
| 6.0 | 98 | 100 | 98 | 97 |

The invention claimed is:

1. A pharmaceutical form consisting essentially of an active substance-containing core which is coated with a partially neutralized, anionic (meth)acrylate copolymer consisting of free radical-polymerized units of 25 to 95% by weight of $C_1$- to $C_4$-alkyl esters of acrylic or methacrylic acid and 5 to 75% by weight of (meth)acrylate monomers having an anionic group, more than 10% of said anionic groups being neutralized by means of a base;
wherein said pharmaceutical form releases at least 30% of the contained active substance in 30 minutes at a pH between 2 and 6 at which the active substance is soluble and stable and at which pH a corresponding pharmaceutical form which is coated with the un-neutralized anionic (meth)acrylate copolymer would release less than 10% of the contained active substance in 30 minutes.

2. The pharmaceutical form as claimed in claim 1, wherein the base which is employed for the partial neutralization has a molecular weight of at most 150.

3. The pharmaceutical form as claimed in claim 1, wherein NaOH, KOH or ammonia is employed for the partial neutralization.

4. The pharmaceutical form as claimed in claim 1, wherein the degree of partial neutralization is more than 10 to 20%.

5. The pharmaceutical form as claimed in claim 4, wherein the pH between 2 and 6 at which at least 30% of the active substance contained is released in 30 minutes and at which the active substance is soluble and stable and at which a corresponding pharmaceutical form which is coated with the un-neutralized anionic (meth)acrylate copolymer would release less than 10% of the active substance contained in 30 minutes lies around 1.5 to 2.5 pH units below the pH of the start of the specific active substance release in intestinal juice or artificial intestinal juice of a not partially neutralized, anionic (meth) acrylate copolymer.

6. The pharmaceutical form as claimed in claim 1, wherein the degree of partial neutralization is more than 20 to 40%.

7. The pharmaceutical form as claimed in claim 6, wherein the pH between 2 and 6 at which at least 30% of the active substance contained is released in 30 minutes and at which the active substance is soluble and stable and at which a corresponding pharmaceutical form which is coated with the un-neutralized anionic (meth)acrylate copolymer would release less than 10% of the active substance contained in 30 minutes lies around 2.5 to 3.5 pH units below the pH of the start of the specific active substance release in intestinal juice or artificial intestinal juice of a not partially neutralized, anionic (meth) acrylate copolymer.

8. The pharmaceutical form as claimed in claim 1, wherein the anionic (meth)acrylate copolymer consists of free radical-polymerized units of 40 to 60% by weight of methacrylic acid and 60 to 40% by weight of methyl methacrylate or 60 to 40% by weight of ethyl acrylate.

9. The pharmaceutical form as claimed in claim 1, wherein the anionic (meth)acrylate copolymer is employed in the form of an aqueous dispersion having a 10 to 50% solids content.

10. The pharmaceutical form as claimed in claim 1, wherein the coating contains up to 50% by weight of an additional film-forming polymer which contains no or only insignificant amounts of ionic side groups.

11. The pharmaceutical form as claimed in claim 10, wherein said additional film-forming polymer which contains no or only insignificant amounts of ionic side groups is selected from the group consisting of a copolymer of methyl methacrylate and ethyl acrylate, a polyvinyl alcohol-polyethylene glycol graft copolymer, polyvinyl acetate, hydroxyethylcellulose, hydroxy-propylcellulose, hydroxypropylmethylcellulose, hydroxy-methylethylcellulose, ethylcellulose, methylcellulose, cellulose esters and mixtures thereof.

12. The pharmaceutical form as claimed in claim 1, wherein the active substance is selected from the group consisting of omeprazole, lanzoprazole, pantoprazole, rabe-prazole, perprazole, esomprazole, tenatoprazole, anastrozole, aripiprazole, dapriprazole, hydroxy-omeprazole, leminoprazole, and paroxetine, pindolol, reboxetine, 5-aminosalicylic acid, sulfasalazine budenoside, natamycin, preglumetacin, sulfasalacine, nitro-furantion, didanosine, acetylsalicylic acid, acemetacin, ibuprofen, diclofenac, naproxen, ketoprofen, dexketoprofen, indometacin, tiaprofenic acid, pravastatin, valproic acid, and ramipril, and salts thereof.

13. The pharmaceutical form as claimed in claim 1, wherein the active substance is a proton pump blocker and the coating is a partially neutralized, anionic (meth)acrylate copolymer of free radical-polymerized units of 40 to 60% by weight of methacrylic acid and 60 to 40% by weight of ethyl acrylate.

14. The pharmaceutical form as claimed in claim 1, wherein the active substance is acetyl salicylic acid and the coating is an anionic (meth)acrylate copolymer, which is partially neutralized to more than 20 to 40%, of free radical-polymerized units of 40 to 60% by weight of methacrylic acid and 60 to 40% by weight of ethyl acrylate.

15. A pharmaceutical form consisting essentially of:
(1) an active substance-containing core, and
(2) a partially neutralized, anionic (meth)acrylate copolymer coating which covers said core and consists of free radical polymerized units of 25 to 95% by weight of $C_1$- to $C_4$-alkyl esters of acrylic or methacrylic acid and 5 to 75% by weight of (meth)acrylate monomers having an anionic group, more than 10% of said anionic groups being neutralized by means of a base;
wherein said pharmaceutical form releases at least 30% of the contained active substance in 30 minutes at a pH between 2 and 6 at which the active substance is adequately soluble and stable and at which pH a corresponding pharmaceutical form which is coated with the un-neutralized anionic (meth)acrylate copolymer would release less than 10% of the contained active substance in 30 minutes.

16. A pharmaceutical form consisting essentially of:
(1) an active substance-containing core, and
(2) a partially neutralized, anionic (meth)acrylate copolymer coating which covers said core and consists of free radical polymerized units of 25 to 95% by weight of $C_1$- to $C_4$-alkyl esters of acrylic or methacrylic acid and 5 to 75% by weight of (meth)acrylate monomers having an anionic group, more than 10% of said anionic groups being neutralized by means of a base;
wherein said pharmaceutical form releases at least 30% of the contained active substance in 30 minutes at a pH between 2 and 6 at which the active substance is soluble and stable and at which pH a corresponding pharmaceutical form which is coated with the un-neutralized anionic (meth)acrylate copolymer would release less than 10% of the contained active substance in 30 minutes.

* * * * *